(12) United States Patent
Wood et al.

(10) Patent No.: US 10,542,964 B2
(45) Date of Patent: Jan. 28, 2020

(54) INTERVENTIONAL MEDICAL DEVICE RETRIEVAL

(71) Applicant: Medtronic, Inc., Minneapolis, MN (US)

(72) Inventors: Rónán Wood, Galway (IE); Lavie Golenberg, Minneapolis, MN (US); Paula McDonnell, Galway (IE)

(73) Assignee: Medtronic, Inc., Minneapolis, MN (US)

( * ) Notice: Subject to any disclaimer, the term of this patent is extended or adjusted under 35 U.S.C. 154(b) by 558 days.

(21) Appl. No.: 15/163,809

(22) Filed: May 25, 2016

(65) Prior Publication Data

US 2017/0340316 A1 Nov. 30, 2017

(51) Int. Cl.
*A61B 17/00* (2006.01)
*A61B 17/50* (2006.01)

(52) U.S. Cl.
CPC ........ *A61B 17/00234* (2013.01); *A61B 17/50* (2013.01); *A61B 2017/00336* (2013.01); *A61B 2017/00358* (2013.01); *A61B 2017/00862* (2013.01); *A61B 2017/00951* (2013.01)

(58) Field of Classification Search
CPC .......... A61B 17/50; A61B 2017/00358; A61B 2017/00623; A61B 2017/22035; A61B 2017/00323; A61B 17/00234; A61F 2002/016; A61F 2002/018; A61M 25/0147
See application file for complete search history.

(56) References Cited

U.S. PATENT DOCUMENTS

| 4,586,923 | A | * | 5/1986 | Gould ............. A61M 25/09033 600/434 |
|---|---|---|---|---|
| 5,417,697 | A | | 5/1995 | Wilk et al. |
| 6,348,056 | B1 | | 2/2002 | Bates et al. |
| 6,605,102 | B1 | | 8/2003 | Mazzocchi et al. |
| 8,066,757 | B2 | | 11/2011 | Ferrera et al. |
| 8,070,791 | B2 | | 12/2011 | Ferrera et al. |
| 8,197,493 | B2 | | 6/2012 | Ferrera et al. |
| 8,364,280 | B2 | | 1/2013 | Marnfeldt et al. |
| 8,574,262 | B2 | | 11/2013 | Ferrera et al. |
| 8,585,713 | B2 | | 11/2013 | Ferrera et al. |
| 8,945,143 | B2 | | 2/2015 | Ferrera et al. |

(Continued)

FOREIGN PATENT DOCUMENTS

WO 2008063156 A2 5/2008

OTHER PUBLICATIONS (PCT/US2017/034233) PCT Notification of Transmittal of the International Search Report and the Written Opinion of the International Searching Authority, dated Aug. 8, 2017, 13 pages.

*Primary Examiner* — Elizabeth Houston
*Assistant Examiner* — Charles M Wei

(57) ABSTRACT

A system for retrieving an implanted medical device includes an outer tubular member and a contractible super-elastic net, which may be joined to an elongate shaft that extends in sliding engagement within the outer tubular member. When the net expands from a contracted condition the net defines a longitudinally extending tubular cavity. An open end of the cavity is sized to receive passage of a housing of the device therethrough; and the net, with the device housing contained therein, forms an interference fit within an inner diameter of the outer tubular member. But, an outer diameter of the net, in a fully expanded condition, is larger than the inner diameter.

11 Claims, 8 Drawing Sheets

(56) References Cited

U.S. PATENT DOCUMENTS

| | | |
|---|---|---|
| 9,126,032 B2 | 9/2015 | Khairkhahan et al. |
| 9,198,687 B2 | 12/2015 | Fulkerson et al. |
| 10,010,437 B2 * | 7/2018 | Bliss .................... A61B 17/221 |
| 2003/0135204 A1 * | 7/2003 | Lee .................... A61B 17/0469 |
| | | 606/1 |
| 2005/0267555 A1 * | 12/2005 | Marnfeldt .......... A61B 17/3417 |
| | | 607/116 |
| 2007/0167974 A1 * | 7/2007 | Cully .................... A61B 17/221 |
| | | 606/200 |
| 2008/0262528 A1 * | 10/2008 | Martin ................. A61B 17/221 |
| | | 606/191 |
| 2009/0209987 A1 * | 8/2009 | Mathews ............. A61B 17/221 |
| | | 606/159 |
| 2011/0288572 A1 * | 11/2011 | Martin ................. A61B 17/221 |
| | | 606/159 |
| 2012/0109148 A1 | 5/2012 | Bonner et al. |
| 2012/0109149 A1 | 5/2012 | Bonner et al. |
| 2012/0165827 A1 * | 6/2012 | Khairkhahan ......... A61N 1/362 |
| | | 606/129 |
| 2013/0031092 A1 | 1/2013 | Bhola et al. |
| 2013/0079758 A1 * | 3/2013 | Goode ................ A61B 17/221 |
| | | 606/1 |
| 2013/0178888 A1 * | 7/2013 | Bliss .................... A61B 17/221 |
| | | 606/200 |
| 2014/0074144 A1 * | 3/2014 | Shrivastava ..... A61B 17/22031 |
| | | 606/200 |
| 2014/0277414 A1 | 9/2014 | Kheradvar |
| 2015/0051610 A1 * | 2/2015 | Schmidt ............. A61N 1/37205 |
| | | 606/129 |
| 2015/0112376 A1 * | 4/2015 | Molaei .................... A61F 2/013 |
| | | 606/200 |
| 2015/133990 A1 | 5/2015 | Davidson |
| 2015/0250578 A1 | 9/2015 | Cook et al. |
| 2015/0283376 A1 | 10/2015 | Ollivier et al. |
| 2015/0335884 A1 | 11/2015 | Khairkhahan et al. |
| 2015/0359547 A1 | 12/2015 | Vale et al. |

* cited by examiner

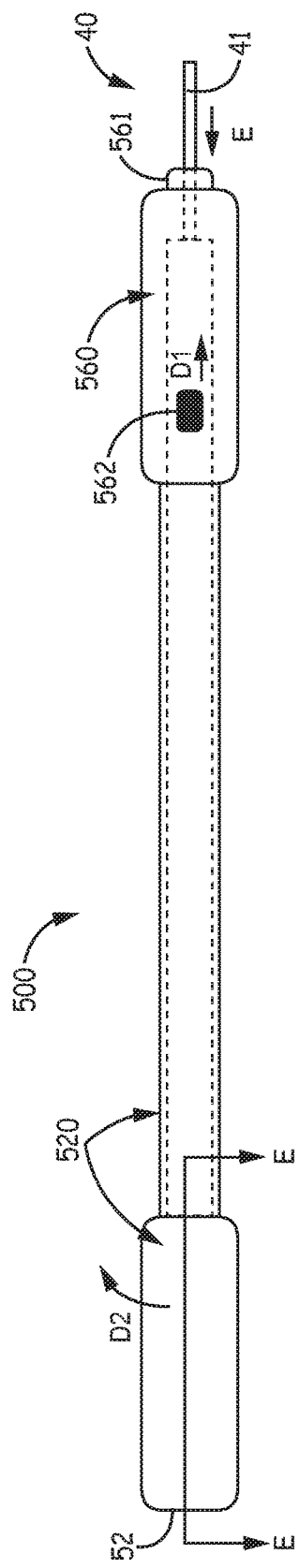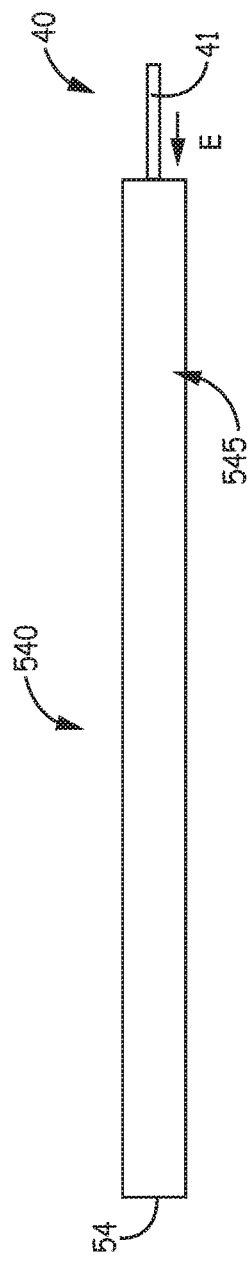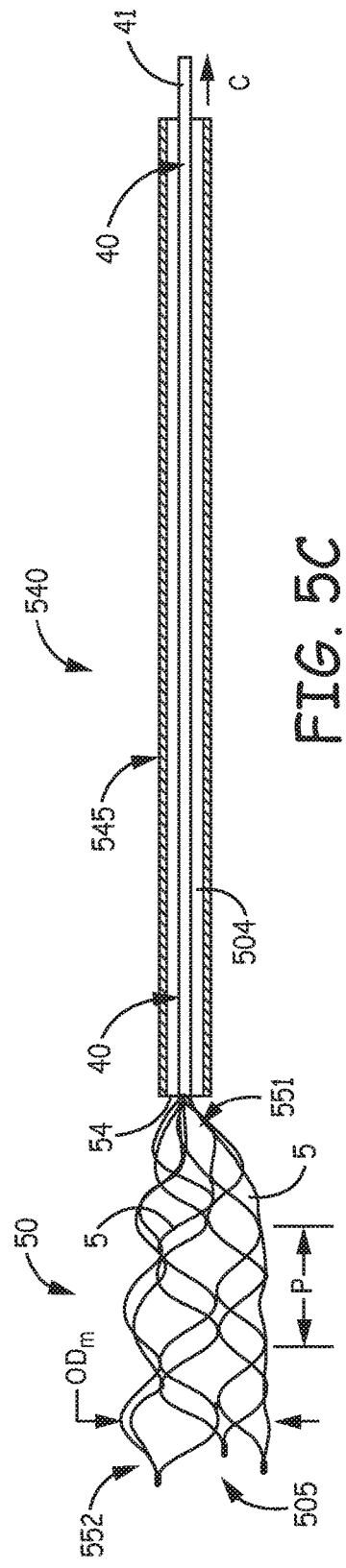

INTERVENTIONAL MEDICAL DEVICE RETRIEVAL

FIELD OF THE DISCLOSURE

The present disclosure pertains to interventional medical systems, and more particularly to systems and methods for retrieving medical devices from implant sites.

BACKGROUND

The traditional implantable cardiac pacemaker includes a pulse generator device to which one or more flexible elongate lead wires are coupled. The device is typically implanted in a subcutaneous pocket, remote from the heart, and each of the one or more lead wires extends therefrom to a corresponding electrode, coupled thereto and positioned at a pacing site, either endocardial or epicardial. Mechanical and/or MRI compatibility issues, sometimes associated with elongate lead wires, are well known to those skilled in the art, and have motivated the development of implantable cardiac pacing devices that are wholly contained within a relatively compact package, the entirety of which is configured for implant in close proximity to the pacing site. FIG. 1 is a schematic diagram that shows potential cardiac implant sites for such a device, for example, within an appendage 102 of a right atrium RA, within a coronary vein CV (via a coronary sinus ostium CSOS), or in proximity to an apex 103 of a right ventricle RV, for example, as shown in FIG. 2.

FIG. 2 shows an exemplary relatively compact implantable medical device 300 having been implanted by an operator using a catheter 200, for example, like the tool described in the commonly assigned United States Patent Application US 2015/0094668, wherein the operator advanced tool 200 into the right heart through the inferior vena cava IVC, for example, from a femoral vein access site, and then deployed device 300 from a device receptacle 230 of catheter 200. In some cases, when it may be necessary to retrieve the implanted device 300, the operator can employ catheter 200 to do so, but new and improved systems and methods would increase the ease and efficiency of retrieval.

SUMMARY

A system for retrieving an implantable medical device from an implant site, according to embodiments disclosed herein, includes an outer tubular member and a contractible super-elastic net, which may be joined to an elongate shaft that extends in sliding engagement within the outer tubular member. When the net expands from a contracted condition, the net defines a longitudinally extending tubular cavity with a closed end and an open end. The open end of the net cavity is sized to receive passage of a housing of the device therethrough; and the net, with the device housing contained therein, forms an interference fit within an inner diameter of the system outer tubular member, the inner diameter being in proximity to a distal-most opening of the outer tubular member. But, when the net is in a fully expanded condition, an outer diameter thereof is larger than the inner diameter. According to some embodiments, the elongate shaft extends in sliding engagement within a retention tube that extends with the outer tubular member, wherein a lumen of the retention tube is sized to hold the net in the contracted condition therein, when the shaft pulls the net into the lumen through a distal opening thereof.

According to some methods disclosed herein, an operator may employ the above-described system to retrieve the implanted medical device as follows. After the operator advances the system to the implant site, so that the distal-most opening of the outer tubular member is located in proximity to the implanted medical device, the operator may advance the super-elastic net out from the distal-most opening, so that the net expands and surrounds the housing of the device. Then the operator may apply a pull force to the expanded net while, at the same time, advancing the outer tubular member over the expanded net, thereby contracting the net around the housing of the device, after which, the operator can apply a pull force to the system to extract the device from the implant site, and then continue to apply the pull force to the contracted net to draw the extracted device into the outer tubular member, through the distal-most opening thereof.

BRIEF DESCRIPTION OF THE DRAWINGS

The following drawings are illustrative of particular embodiments of the present invention and therefore do not limit the scope of the invention. The drawings are not to scale (unless so stated) and are intended for use in conjunction with the explanations in the following detailed description. Embodiments will hereinafter be described in conjunction with the appended drawings wherein like numerals denote like elements, and:

FIG. 5A is a plan view of a system, according to some embodiments;

FIGS. 5B-C are plan views of a retrieval assembly of the system, separate from a remainder of the system, in two conditions, according to some embodiments;

DETAILED DESCRIPTION

The following detailed description is exemplary in nature and is not intended to limit the scope, applicability, or configuration of the invention in any way. Rather, the following description provides practical examples, and those skilled in the art will recognize that some of the examples may have suitable alternatives.

Figure 1:
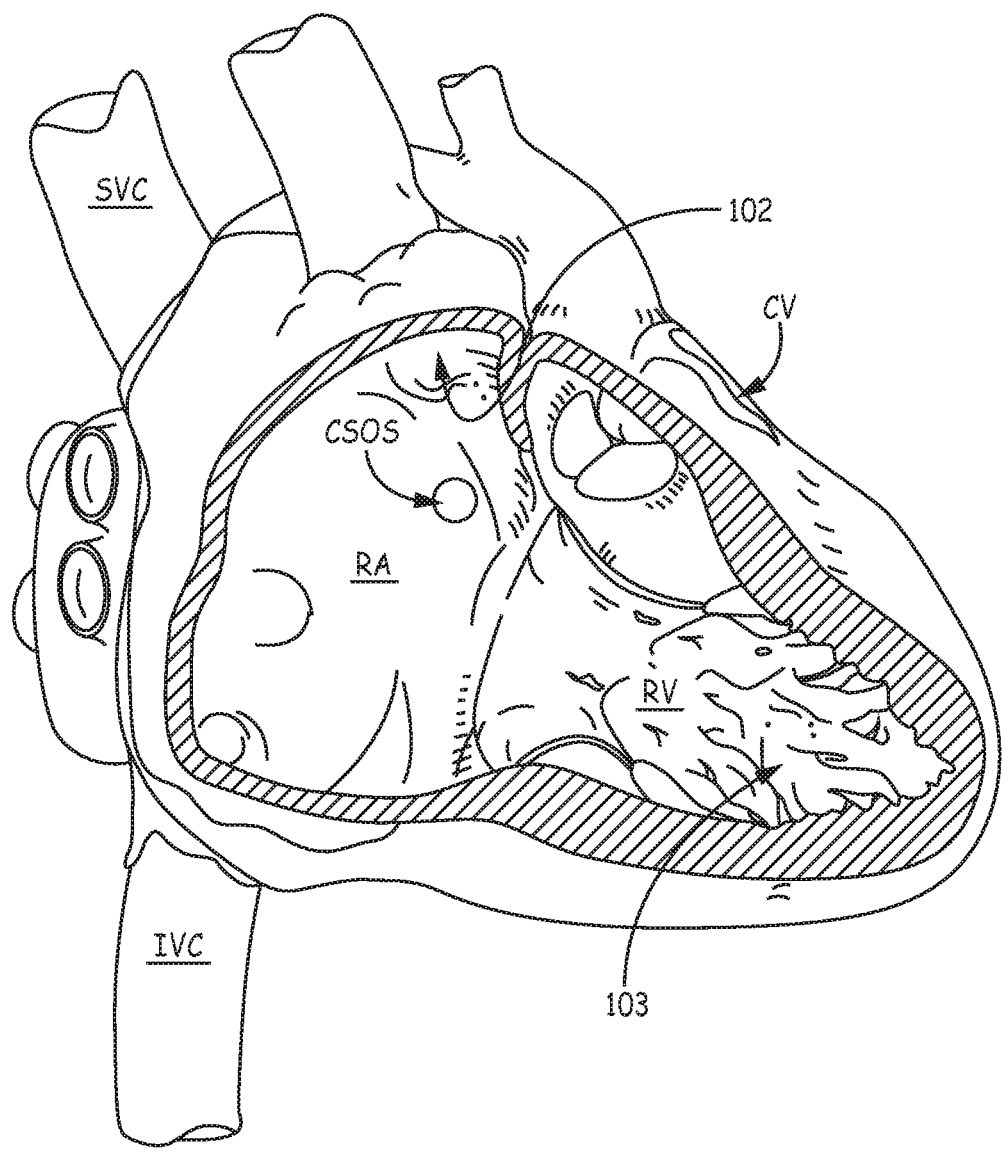
FIG. 1 is a schematic diagram showing potential implant sites for a relatively compact implantable medical device.
Figure 2:
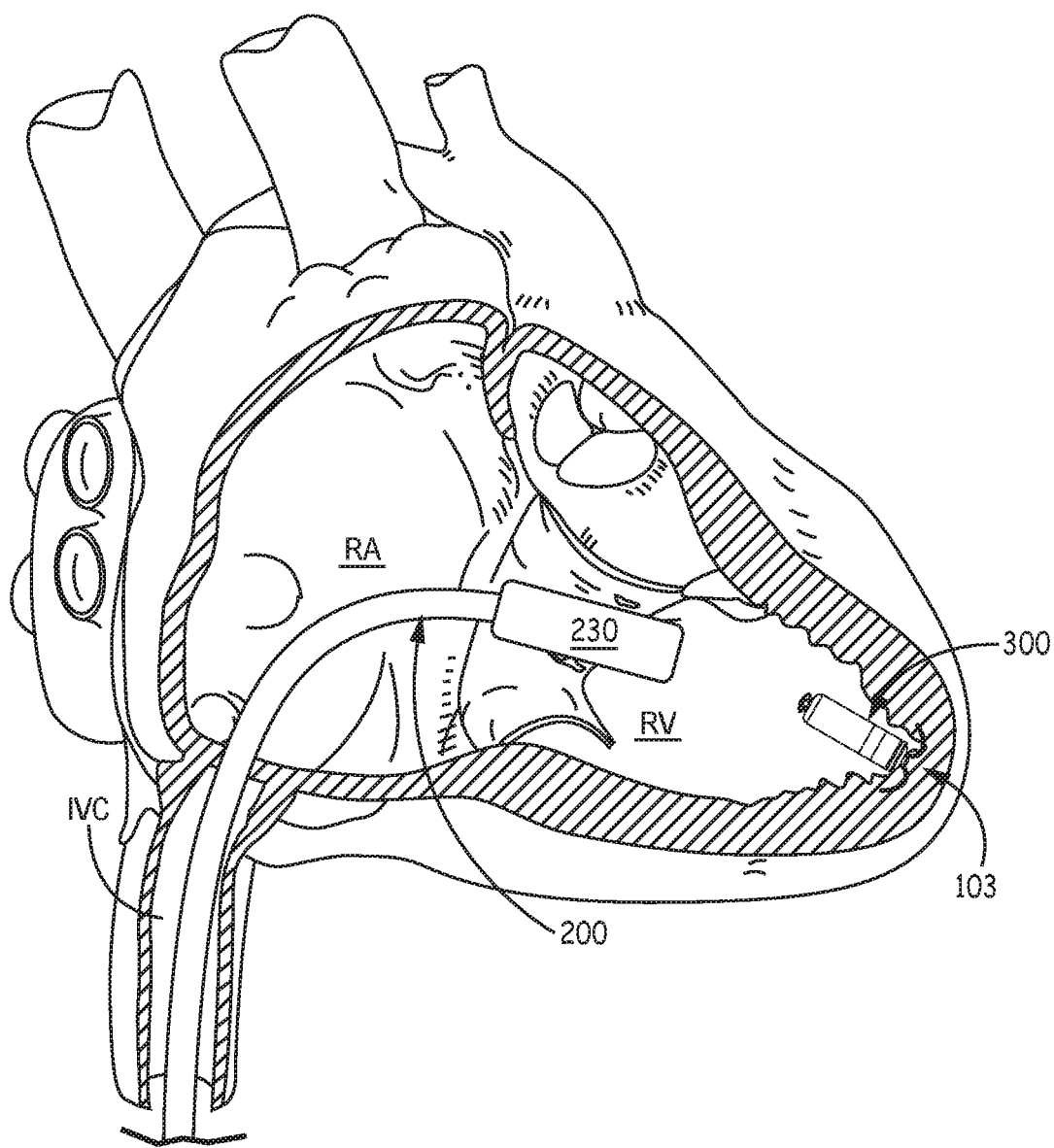
FIG. 2 is a schematic showing an exemplary relatively compact implantable medical device having been delivered from a catheter to an implant site.
Figure 3:
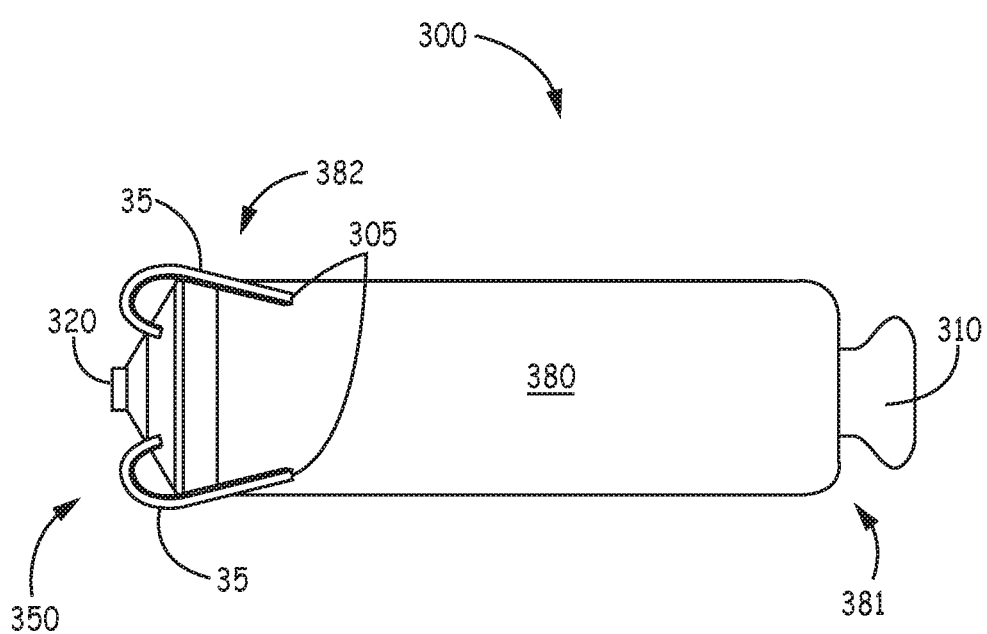
FIG. 3 is a plan view of the exemplary relatively compact implantable medical device, according to some embodiments.

FIG. 3 is a plan view of implantable medical device 300, according to some embodiments. FIG. 3 illustrates device 300 including a hermetically sealed housing 380 extending from a proximal end 381 thereof to a distal end 382, wherein an electronic controller (not shown), for example, a pulse generator and an associated power supply, is contained in housing 380. Device 300 further includes an electrode 320 and a fixation member 350, both mounted in proximity to distal end 382 of housing 380, wherein electrode 320 is electrically coupled to the controller via a hermetically sealed feedthrough assembly (not shown) such as is known in the art. Housing 380, for example, formed from a biocompatible and biostable metal such as titanium, may be overlaid with an insulative layer, for example, medical grade polyurethane, parylene, or silicone, and device 300 may include another electrode (not shown), for example, formed by removing a portion of the insulative layer to expose the metallic surface of housing 380. The other electrode may function in conjunction with electrode 320 for bipolar pacing and sensing, when fixation member 350 secures electrode 320 in intimate tissue contact at a target implant site. FIG. 3 further illustrates device 300 including an optional snare feature 310 joined to proximal end 381 of housing 380, wherein feature 310 is configured for snaring, for example, by an elongate snare member 42, which is described below in conjunction with FIG. 4.

With further reference to FIG. 3, device fixation member 350 includes a plurality of fingers 35 spaced apart from one another around a perimeter of device housing distal end 382, wherein fingers 35 are configured to fix device 300 to tissue at an implant site. Although only two fingers 35 of fixation member 350 are shown in FIG. 3, fixation member 350 may include as many as eight fingers 35. According to an exemplary embodiment, fixation fingers 35 are integrally formed with one another, having been cut from Nitinol tubing, according to methods known in the art. After cutting the Nitinol tubing, fingers 35 may be shaped by bending and holding fingers 35 in the illustrated curvature while heat treating, according to methods known to those skilled in the art. Fixation member 350 may be mounted to distal end 382 of device housing 380, for example, in a manner similar to that described for a fixation component 102 in co-pending and commonly assigned United States Patent Application 2012/0172690, which description is hereby incorporated by reference. The super-elastic nature of Nitinol allows fingers 35 to elastically deform between a relaxed condition, which is shown, and an extended condition, in which a free end 305 of each finger extends distally away from distal end 382 of device housing 380, for example, as shown in FIG. 6D.

Figure 4:
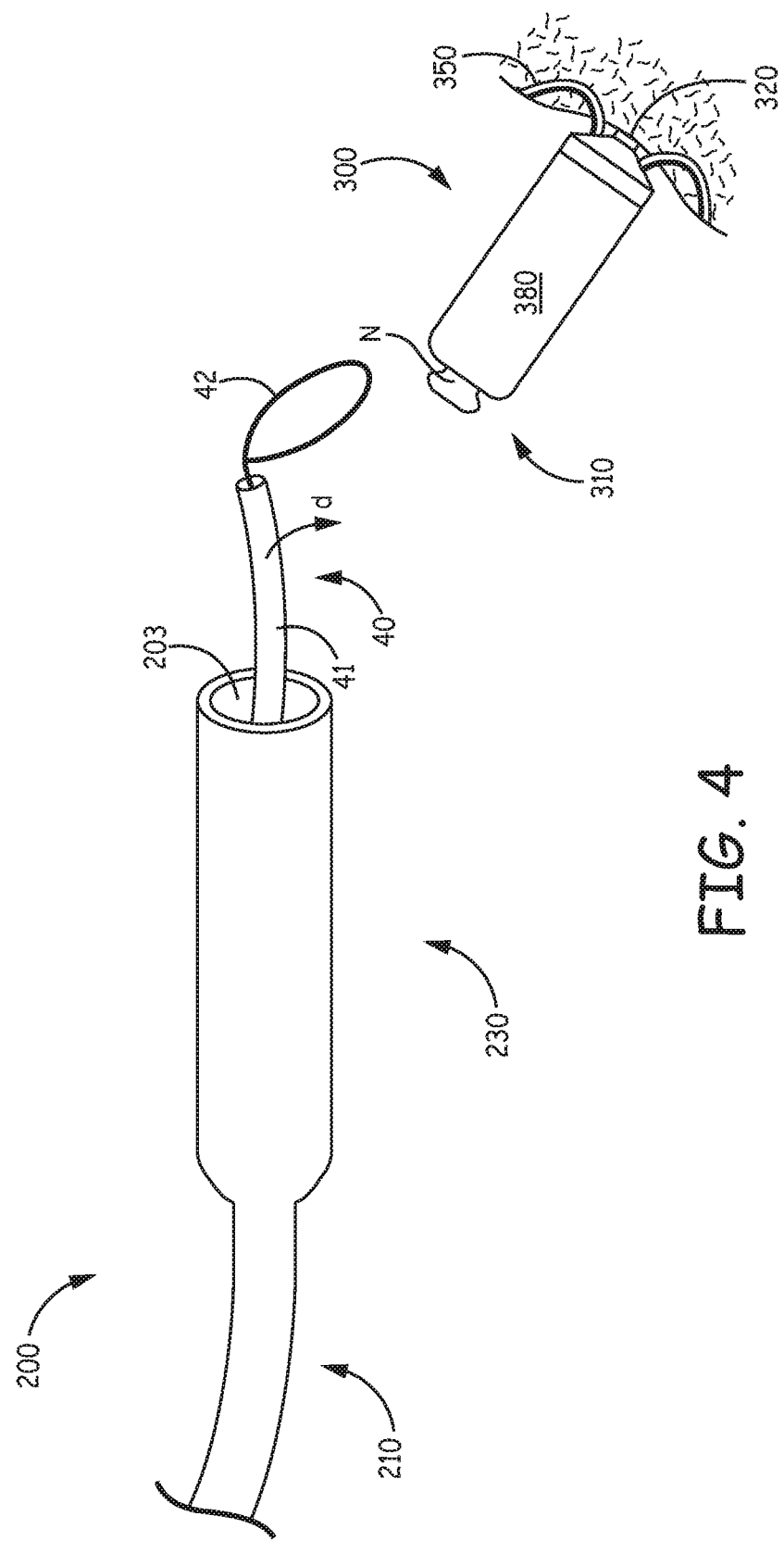
FIG. 4 is a schematic for describing some difficulties in retrieving the medical device from an implant site.

FIG. 4 is a schematic for describing some difficulties in retrieving medical device 300 from an implant site. FIG. 4 illustrates device receptacle 230 of catheter 200 having been advanced to the implant site, and a device retrieval tool 40 having been passed out through a distal-most opening 203 of receptacle 230. Retrieval tool 40 includes elongate snare member 42, which extends within a shaft 41 of tool 40, wherein snare member 42 may be a medical grade Nitinol wire slideably engaged within shaft 41 to open and close a loop thereof. Snare member 42 is shown deployed, and the operator may deflect, per arrow d, shaft 41, via a steering assembly thereof, to maneuver the deployed snare member 42 into position around a neck N of device snare feature 310. But the operation of tool 40 may be somewhat tedious and time consuming, particularly if the operator inadvertently engages snare member 42 around device housing 380, rather than around neck N of snare feature 310. Furthermore, once the operator has successfully engaged snare member 42 around snare feature neck N, the snared device 300 may be so misaligned with distal-most opening 203 of receptacle 230, that extracting device 300 from the implant site and drawing device 300 into receptacle 230 may be somewhat difficult. Embodiments of the present invention disclosed herein are configured to overcome these difficulties in retrieving implanted medical devices like device 300.

FIG. 5A is a plan view of a system 500, according to some embodiments; and FIGS. 5B-C are plan views of a retrieval assembly 540 of system 500, separate from a remainder of the system 500, in two conditions, according to some embodiments. FIG. 5A illustrates system 500 including an elongate outer tubular member 520, which may be coupled to a handle 560, and retrieval assembly 540, denoted with dashed lines in FIG. 5A, which extends within a lumen 502 of tubular member 520—lumen 502 may be seen in the cross-section view of FIG. 5E. FIGS. 5B-C illustrate retrieval assembly 540 including a shaft 40, a contractible super-elastic net 50 joined to shaft 40, and a retention tube 545, which has a lumen 504 in which shaft 40 extends in sliding engagement. Retention tube 545 is preferably formed from a flexible medical grade polymer, for example, polyether block amide, such as PEBAX® 7233, or high density polyurethane. FIG. 5B illustrates net 50 being held within retention tube lumen 504 in a contracted condition; and FIG. 5C illustrates net 50 expanded outside lumen 504, in a relaxed, or completely unconstrained condition. With reference to FIG. 5B, moving shaft 40 per arrow E pushes net 50 out though a distal opening 54 of lumen 504 so that net 50 expands; and, with reference to FIG. 5C, moving shaft 40 per arrow C pulls net 50 back through distal opening 54 and into the contracted condition of FIG. 5B.

Figure 5D:
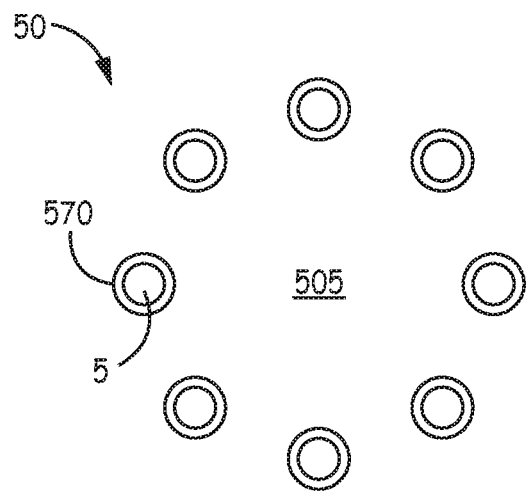
FIG. 5D is a cross-section view of a portion of the retrieval assembly, according to some embodiments.

FIG. 5C further illustrates expanded super-elastic net 50 defining a tubular cavity 505 that extends longitudinally from a closed end 551 thereof to an open end 552 thereof. FIG. 5C illustrates shaft 40 of retrieval assembly 540 joined to net 50 in proximity to closed end 551 of cavity 505, wherein shaft 40 may be formed from a resilient wire or a hypo-tube (e.g. medical grade stainless steel). According to some embodiments, net 50 is formed by a plurality of super-elastic wires 5 (e.g. Nitinol) spaced apart from one another around cavity 505, wherein each wire 5 may extend along a sinusoidal path, and adjacent wires 5 may be welded together at locations where the paths thereof touch, for example, as shown in FIG. 5C. Eight wires 5 may thus form net 50, and a pitch P of each of the paths thereof may be about 8 mm, according to an exemplary embodiment. According to some alternate embodiments, net 50 is cut from a tube of super-elastic material (e.g., Nitinol), according to methods known in the art. In some embodiments, retrieval assembly 540 further includes a relatively tacky material (e.g., a relatively soft medical grade polymer, such as silicone rubber), which lines at least an interior surface of net 50, for example, as illustrated in FIG. 5D. FIG. 5D is a cross-section view of net 50, according to some embodiments, wherein a coating 570 around each super-elastic wire 5 is formed from the relatively tacky material. Although wires 5 are shown having a circular cross-section, other cross-section shapes, for example, elliptical or generally rectangular, are not outside the scope of the present invention.

With reference back to FIG. 5A, lumen 502 of outer tubular member 520 is in fluid communication with a proximal port opening 561 of handle 560, and a proximal end 41 of retrieval assembly shaft 40 is shown extending out from opening 561 and, thus, accessible to an operator of system 500. Furthermore, lumen 502 extends longitudinally to a terminating distal-most opening 52, out from which retrieval assembly net 50 may be advanced. According to some embodiments, retention tube 545 of retrieval assembly 540 is fixed to system handle 560, while, according to some alternate embodiments, retention tube 545 is moveable relative to handle 560. In the latter, alternate embodiments, an entirety of retrieval assembly 540 may be provided to an operator separate from a remainder of system 500, so that the operator can insert assembly 540 into outer tubular member 520, for example, after using system 500 to deliver device 300 to an implant site, from lumen 502 of outer tubular member 520, through distal-most opening 52. According to an exemplary embodiment, retention tube lumen 504 has a diameter of about 0.032 inch.

Figure 5E:
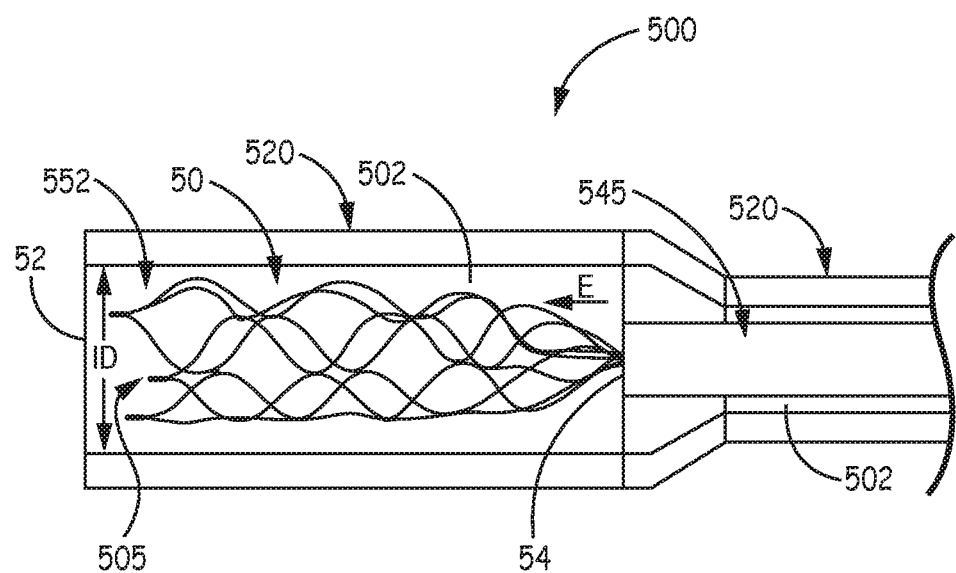
FIG. 5E is a cross-section view through section line E-E of FIG. 5A, according to some embodiments.

With further reference to FIG. 5C, a maximum outer diameter $OD_m$ of net 50, when in a fully expanded condition (completely unconstrained), is greater than an inner diameter ID of outer tubular member 520 in proximity to distal-most opening 502 (FIGS. 5E, 6A), according to some preferred embodiments. According to an exemplary embodiment, maximum outer diameter $OD_m$ is about 0.059 inch. FIG. 5E is a cross-section view through section line E-E of FIG. 5A, according to some embodiments, when an operator has advanced retrieval assembly net 50 out through distal opening 54 of retention tube 545, for example, by pushing proximal end 41 of shaft 40, per arrow E (FIG. 5A). FIG. 5E shows net 50 partially expanded, being constrained from full expansion by inner diameter ID of outer tubular member 520. Further advancement of net 50 out through distal-most opening 52 of tubular member 520 will allow net 50 to fully expand to the completely unconstrained condition, for example, as shown in FIG. 5, or to the unconstrained condition that is shown in FIG. 6A.

Figure 6A:
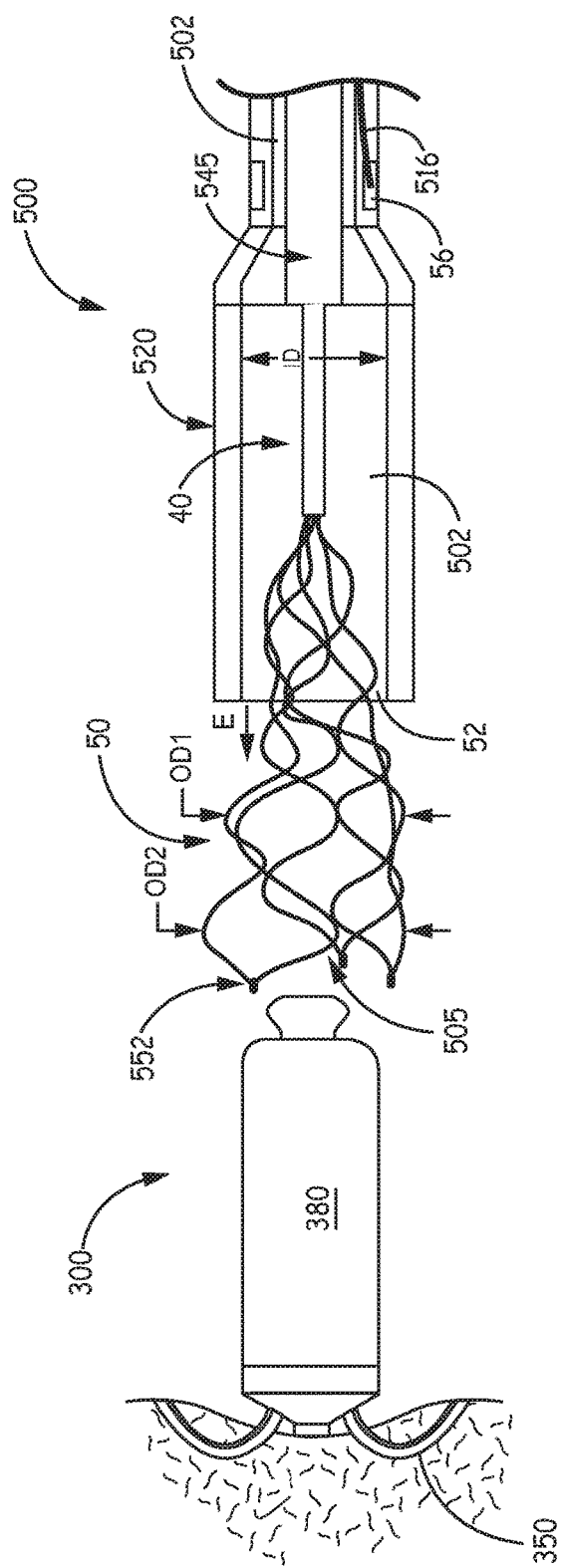
FIGS. 6A-D are schematics outlining some methods.

FIG. 6A is the first of a series of schematics that outline some methods for retrieving the implanted medical device 300 with system 500. FIG. 6A illustrates system 500 having been advanced by the operator to the implant site so that distal-most opening 52 is located in proximity to implanted device 300. In some preferred embodiments, system 500 further includes a steering assembly, for example, as illustrated in FIGS. 5A and 6A, to help the operator navigate to the implant site and locate distal-most opening 52 for the retrieval of device 300. According to the illustrated embodiment, the steering assembly includes a pull band 56, shown mounted to outer tubular member 520, an actuator 562, shown mounted to handle 560, and an elongate pull wire 516, which extends along a length of tubular member 520. Pull wire 516 has a distal end coupled to pull band 56 and a proximal end coupled to actuator 562, so that moving actuator 562 per arrow D1 causes pull wire 516 to deflect tubular member 520 per arrow D2. FIG. 6A shows super-elastic net 50 advanced out from distal-most opening 52 and expanded, as described above, so that the operator can further advance net 50 around device housing 380, for example, as shown in FIG. 6B.

FIG. 6A further illustrates an embodiment of net 50 that has an outward tapering outer diameter at open end 552 of net cavity 505, for example, increasing from a first diameter OD1 to a second diameter OD2. The outward tapering may facilitate alignment of cavity open end 552 with implanted device 300. Whether the outer diameter of net 50 tapers outward, or not (FIG. 5C), open end 552 of net cavity 505 is sized to receive passage of device housing 380 therethrough, with ample clearance, when the operator advances net 50 out through distal-most opening 52.

Figure 6B:
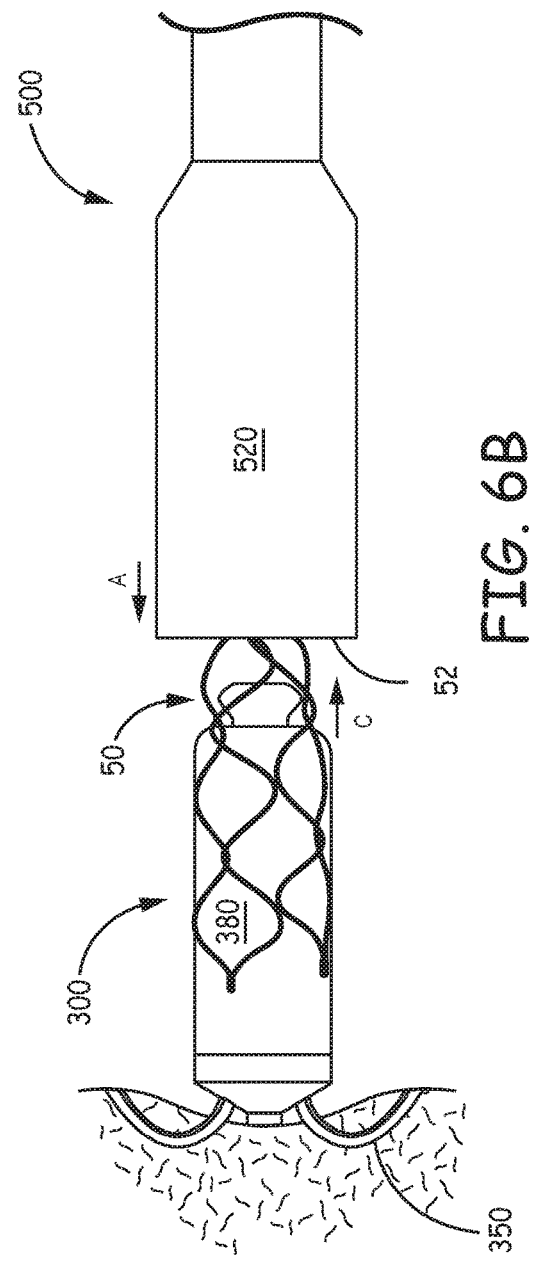

FIG. 6B shows outer tubular member 520 being advanced by the operator, per arrow A, to track over shaft 40 and net 50, while the operator applies a pull force, per arrow C, to net 50. The pull force applied to net 50, in combination with advancing, or pushing outer tubular member 520, contracts and locks net 50 around device housing 380. Net cavity 505 is sized to contain enough of a length of device housing 380 to create a friction fit thereabout, when net 50 contracts, for example, being about 12 mm long in some embodiments. As described above, the tacky material that may line the inner surface of net 50 (e.g. coating 570 around each super-elastic wire 5 shown in FIG. 5D) further enhances the locking of net 50 around device housing 380 by increasing the friction at the interface therebetween. As the operator continues to apply the combined pushing of outer tubular member 520 and pulling of net 50, device 300 can be extracted from the implant site and drawn into lumen 502 of outer tubular member 520 through distal-most opening 52, as shown in FIGS. 6C-D.

Figure 6C:
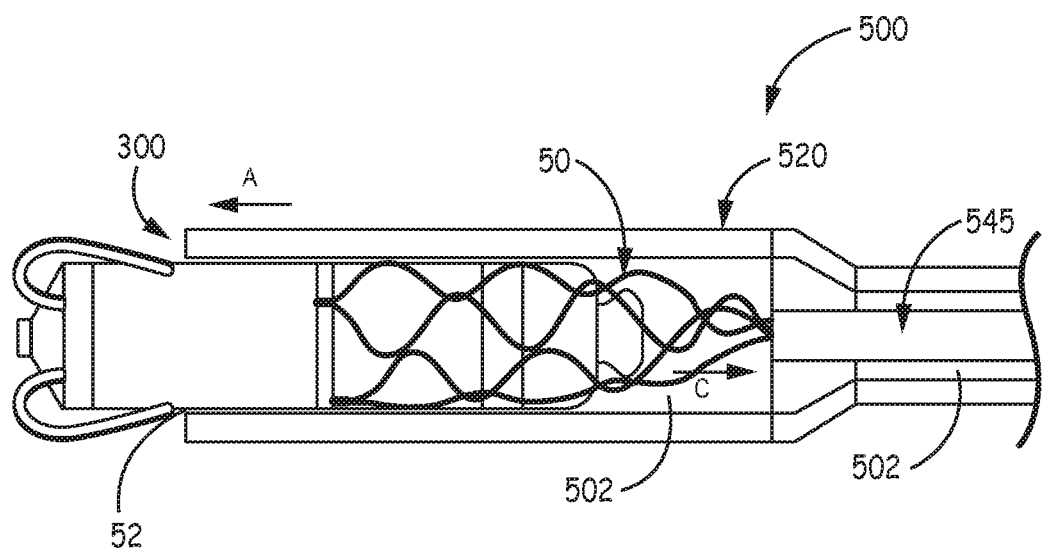
Figure 6D:
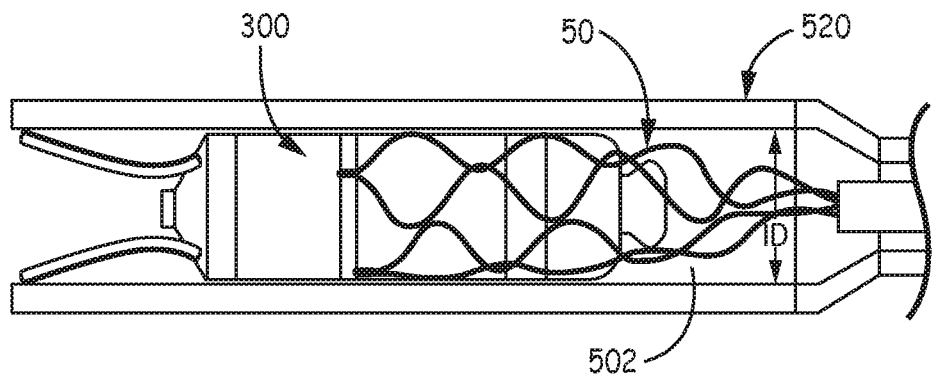

Net 50, with device housing 380 contained therein, as shown in FIGS. 6C-D, preferably forms an interference fit with inner diameter ID of tubular member 520; and, with reference back to FIG. 5D, a diameter of wires 5, with coating 570 may be about 0.009 inch for the illustrated embodiment. It should be noted that according to some alternate embodiments, retrieval assembly 540 need not include retention tube 545 so that shaft 40 and super-elastic net 50 interface directly with outer tubular member 520, which retains net 50 in lumen 502. According to an exemplary embodiment, inner diameter ID of outer tubular member 520 is about 0.3 inch (7.6 mm), and, as illustrated, may extend over a limited length (e.g., about 31 mm) in proximity to distal-most opening 52, with lumen 502 being smaller (e.g., about 0.154 inch (3.9 mm)) along a proximal length (e.g., about 100 cm) of outer tubular member 520. The proximal length of outer tubular member 520 may be formed by a stainless steel braid-reinforced medical grade polymer, for example, one or more appropriate grades of polyether block amide, which are arranged for decreasing stiffness from handle 560 distally (e.g., PEBAX® 3533, 6333, 4033, and 7233); and the distal portion of outer tubular member 520, which is terminated by distal-most opening 52, may be formed from a medical grade polyether block amide (e.g., PEBAX® 7233 SA-01)), and preferably includes a radiopaque marker band (not shown) integrated therein.

In the foregoing detailed description, the invention has been described with reference to specific embodiments. However, it may be appreciated that various modifications and changes can be made without departing from the scope of the invention as set forth in the appended claims.

We claim:

1. A system for retrieving an implantable medical device, comprising:

the implantable medical device, wherein the device comprises an electronic controller, a hermetically sealed housing containing the controller and extending over a length from a proximal end thereof to a distal end thereof, and a fixation member mounted to the housing distal end for fixing the device to tissue at the implant site;

an elongate outer tubular member including a longitudinally extending lumen, the lumen terminating in a distal-most opening that allows passage of the medical device therethrough, and an inner diameter of the lumen in proximity to the distal-most opening being sized to contain the medical device therein;

a steering assembly including a pull band mounted to the elongate outer tubular member and coupled to an elongate pull wire extending through the elongate outer tubular member, wherein actuation of the elongate pull wire results in a deflection of the elongate outer tubular member in a first direction; and a retrieval assembly comprising:

a contractible super-elastic net, the net defining a longitudinally extending tubular cavity when the net expands from a contracted condition thereof, the cavity extending between a closed end thereof and an open end thereof, the open end of the cavity being sized to receive passage of the device housing therethrough, and the net, when in a fully expanded condition, having an outer diameter larger than the inner diameter of the elongate outer tubular member in proximity to the distal-most opening;

an elongate shaft joined to the net in proximity to the closed end thereof; and an elongate retention tube including a lumen, in which the shaft extends in sliding engagement, the retention tube extending within the lumen of the elongate outer tubular member of the system and including a distal opening, wherein, in response to a pull force applied to the net via the shaft in combination with advancing the outer tubular member to track over the shaft and to come into contact with the net, the net is configured to contract and lock around the device housing, wherein the retention tube lumen is sized to hold the net in the contracted condition therein, when the shaft pulls the net into the retention tube lumen through the retention tube distal opening thereof, and wherein the net, with the device housing contained therein, forms an interference fit within the inner diameter of the elongate outer tubular member.

2. The system of claim 1, wherein the retrieval assembly further comprises a medical grade polymer lining at least an interior surface of the super-elastic net.

3. The system of claim 1, wherein the retrieval assembly super-elastic net comprises a plurality of super-elastic wires spaced apart from one another around the net cavity, each wire extending along a sinusoidal path.

4. The system of claim 3, wherein each wire of the plurality of super-elastic wires comprises a coating of a medical grade polymer.

5. The system of claim 1, wherein the retrieval assembly super-elastic net comprises a laser cut super-elastic tube.

6. The system of claim 1, wherein the outer diameter of the retrieval assembly super-elastic net tapers outward at the open end of the cavity.

7. A system for retrieving an implantable medical device, comprising:

the implantable medical device, wherein the device comprises an electronic controller, a hermetically sealed housing containing the controller and extending over a length from a proximal end thereof to a distal end thereof, and a fixation member mounted to the housing distal end for fixing the device to tissue at the implant site;

an elongate outer tubular member including a longitudinally extending lumen, the lumen terminating in a distal-most opening that allows passage of the medical device therethrough, and an inner diameter of the lumen in proximity to the distal-most opening being sized to contain the medical device therein;

a steering assembly including a pull band mounted to the elongate outer tubular member and coupled to an elongate pull wire extending through the elongate outer tubular member, wherein actuation of the pull wire results in a deflection of the elongate outer tubular member in a first direction; and a retrieval assembly comprising:

a contractible super-elastic net, the net defining a longitudinally extending tubular cavity when the net expands from a contracted condition thereof, the cavity extending between a closed end thereof and an open end thereof, the open end of the cavity being sized to receive passage of the device housing therethrough, and the net, when in a fully expanded condition, having an outer diameter larger than the inner diameter of the elongate outer tubular member in proximity to the distal-most opening;

a medical grade polymer lining at least an interior surface of the super-elastic net; and an elongate shaft joined to the net in proximity to the closed end thereof, the shaft extending in sliding engagement within the lumen of the elongate outer tubular member of the system;

wherein, in response to a pull force applied to the net via the shaft in combination with advancing the outer tubular member to track over the shaft and to come into contact with the net, the net is configured to contract and lock around the device housing, and wherein the net, with the device housing contained therein, forms an interference fit within the inner diameter of the elongate outer tubular member.

8. The system of claim 7, wherein the retrieval assembly super-elastic net comprises a plurality of super-elastic wires spaced apart from one another around the net cavity, each wire extending along a sinusoidal path.

9. The system of claim 8, wherein the medical grade polymer of the retrieval assembly comprises a coating around each wire of the plurality of super-elastic wires.

10. The system of claim 7, wherein the retrieval assembly super-elastic net comprises a laser cut super-elastic tube.

11. The system of claim 7, wherein the outer diameter of the retrieval assembly super-elastic net tapers outward at the open end of the cavity.

* * * * *